United States Patent [19]

Ricci et al.

[11] 4,329,425

[45] May 11, 1982

[54] METHOD FOR DETERMINATION OF TRANSAMINASES AND RELATIVE DIAGNOSTIC KIT

[75] Inventors: Giorgio Ricci; Giorgio Federici, both of Rome, Italy

[73] Assignee: Biodata S.p.A., Italy

[21] Appl. No.: 168,286

[22] Filed: Jul. 10, 1980

[30] Foreign Application Priority Data

Jul. 17, 1979 [IT]   Italy ............................... 49789 A/79

[51] Int. Cl.$^3$ ............................................. C12Q 1/52
[52] U.S. Cl. ........................................ 435/16; 435/15; 435/26; 435/810
[58] Field of Search ...................... 435/15, 16, 26, 810

[56] References Cited

U.S. PATENT DOCUMENTS

| | | | |
|---|---|---|---|
| 3,206,376 | 9/1965 | Babson | 435/16 |
| 3,746,625 | 7/1973 | Bergmeyer | 435/26 |
| 3,819,488 | 6/1974 | Rush et al. | 435/26 |
| 4,017,365 | 4/1977 | Nakayama et al. | 435/26 |
| 4,241,179 | 12/1980 | Madappally et al. | 435/16 |

OTHER PUBLICATIONS

Chemical Abstracts, 91:170694a, Nov. 1979.
Chemical Abstracts, 87:128969m, Oct. 1977.

*Primary Examiner*—Peter A. Hruskoci
*Attorney, Agent, or Firm*—Ostrolenk, Faber, Gerb & Soffen

[57] ABSTRACT

A kinetic UV method of determining GOT and GPT by reacting transaminase with a substrate uses L-cysteinsulfinic acid and L-alanine as the substrate and lactic dehydrogenase as the revealing enzyme.

4 Claims, No Drawings

METHOD FOR DETERMINATION OF TRANSAMINASES AND RELATIVE DIAGNOSTIC KIT

The present invention relates to a method for determination of transaminases for use in the field of clinical diagnoses.

Transamination means the process of transferring an aminogroup from an aminoacid to a keto-acid. Enzymes which catalyze this type of reaction are named transaminases and their determination has become essential in clinical chemistry since 1954 when, LaDue, Wroblewski and Karmen communicated that GOT (Glutamic Oxalacetic Transaminase, or Aspartate Amino Transferase or EC 2.6.1.1. according to I.U.B. classification) increases after myocardial infarction. Variations have been noted substantially of both GOT and GPT (Glutamic Pyruvic Transaminase, or Alanine Amino Transferase or EC 2.6.1.2. according to I.U.B. classification) under other pathologic forms, especially in hepathopathies.

GOT catalyzes the following reaction:

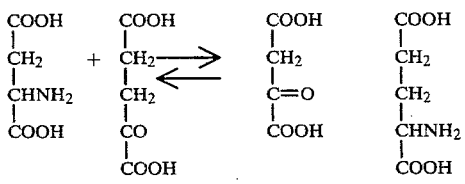

Aspartic acid α-ketoglutaric ac. Oxalacetic acid Glutamic acid while GPT catalyzes the following reaction.

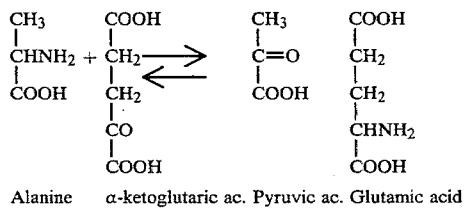

Alanine   α-ketoglutaric ac. Pyruvic ac. Glutamic acid

In the case of GOT, it is not easy to determine the aspartic and the α-ketoglutaric acid; therefore, all methods actually in use are based on the determination of oxalacetic acid, either directly or indirectly.

All over the world two methods are employed:

(1) The colorimetric method based on the reaction of oxalacetic acid with 2,4-dinitrophenylhydrazine; this reaction is not kinetic, but after a pre-established period of incubation the quantity of keto-acid formed is dosed by measuring at 536 nm the extinction of the formed phenylhydrazone. This method, although modified in the course of the years, still presents drawbacks in the case of samples of icteric people.

(2) The kinetic U.V. method is that generally considered as the reference method due to its high accuracy and specificity.

The oxalacetic acid produced in the transamination reaction is determined through an enzymatic reaction coupled with malic dehydrogenase (MDH) by measuring at 340 nm the oxidation of NADH (Nicotinamide Adenin Dinucleotide in the reduced form).

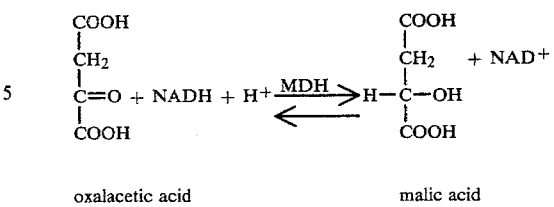

oxalacetic acid           malic acid

The modifications made to this method first introduced by Karmen permitted the reaction to be optimized as a function of the concentration of substrate and of the determination temperatures, and the troubles due to the non linear kinetic phases to be overcome.

Also for GPT, similar considerations can be made in the case of the Colorimetric test, while the kinetic U.V. method introduced by Henley and Pollard is based on the determination of pyruvic acid formed in the reaction of alanine transamination by an enzymatic reaction couple with the lactic dehydrogenase (LDH), the reoxidation of the NADH being measured at 340 nm.

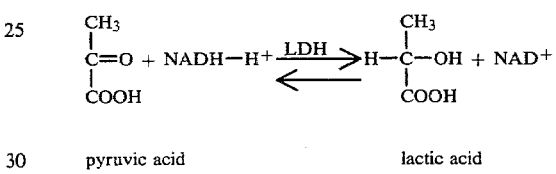

pyruvic acid           lactic acid

Also for the kinetic U.V. method, the modifications introduced and described in the literature permitted the reaction to be optimized as a function of the concentrations of substrate and of the determination temperatures.

The determination of GOT and GPT activities present in the serum, or in other biological samples is effected through the colorimetric or U.V. kinetic methods mentioned above. This always requires to the analyst to carry out two different analyses for the two transaminases. This is due to the technical impossibility of coupling the two U.V. kinetic enzymes mentioned above in one determination, because of the cross-inhibition phenomena.

The object of the present invention is a new method which permits to determine spectrophotometrically, in U.V. kinetic, with one only assay, the sum of the two transaminases activities, and thus constitutes the first screening assay between normal and pathological values of such enzymatic activities. In addition, according to the analyst requirements, the new method permits, by simply modifying the order of introduction of reactives and substrates in the reaction mixture, to exactly determine the actvities of the two transaminases, in Units per liter, in the same sample of plasma or serum, thus saving time with respect to the methods traditionally used in laboratory.

It is known that GOT is able to catalyze transamination not only of its natural substrates (glutamic acid and aspartic acid), but also, of other aminoacids. Among these, the cysteinsulfinic acid is also actively transaminated, in the presence of α-ketoglutaric acid, with formation of β-sulfinyl pyruvic acid, which, being unstable in water solution, is quickly hydrolyzed to pyruvic acid and sulfite, according to the following reaction scheme:

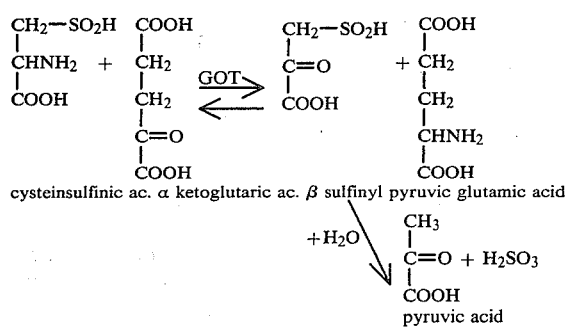

cysteinsulfinic ac.   α ketoglutaric ac.   β sulfinyl pyruvic   glutamic acid
pyruvic acid Even in the absence of α-ketoglutaric acid, GOT is able to interreact with cysteinsulfinic acid and catalyze an α-β elimination reaction according to the following scheme:

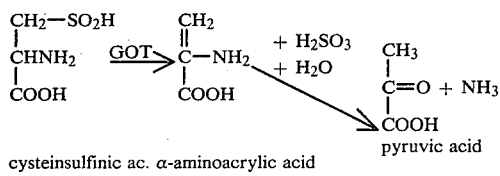

cysteinsulfinic ac.   α-aminoacrylic acid   pyruvic acid

Also in this case, the final product of the reaction is pyruvic acid, and the activity of GOT may be determined in spectrophotometric kinetic at 340 nm by measuring the re-oxidation of NADH in the presence of lactic dehydrogenase, the same enzyme employed for determination of GPT activity.

The use of the cysteinsulfinic acid as the substrate of GOT thus permits employing only one revealing enzyme, the lactic dehydrogenase (LDH), in the coupled determination of the two transaminases, according to the following scheme:

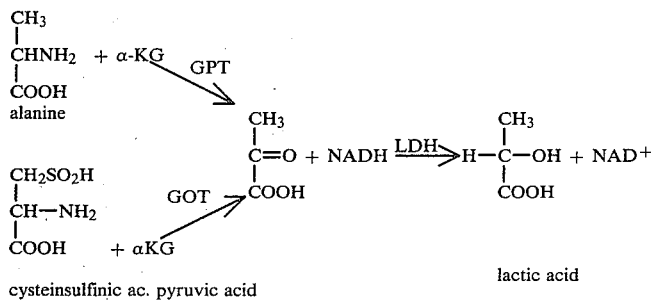

cysteinsulfinic ac.   pyruvic acid   lactic acid

The decrease of extinction at 340 nm represents a measure of the quantity of the pyruvic acid produced and, as a consequence, of the activities of both transaminases. It is important to note that the simultaneous determination of transaminases is possible in these conditions thanks to the absence of cross-inhibition between the substrates employed. The particular kinetic properties of the reaction between GOT and cysteinsulfinic acid consent two different applications of the system, as illustrated in the following examples:

EXAMPLE 1

Method of determination of GOT and GPT absolute activities

To a reaction mixture of 2.5 ml containing L-alanine (200 mM), α-ketoglutaric acid (2 mM), β-NADH (0.24 mM) and 3.6. units of lactic dehydrogenase in Tris-HCl buffer (80 mM), pH 8.5, 0.5 ml plasma or serum are added, then the decrease of extinction is measured at 340 nm (or at other wave lengths, e.g., 334 or 365 nm, according to the instrument employed). The decrease is in direct relationship to the amount of transformation of alanine to pyruvic acid as caused by GPT. After a few minutes of reaction, 0.1 ml of a solution of cysteinsulfinic acid are added, so that the final concentration in the reaction mixture is 66 mM. The increase Δ E/min is due, in this case, to the transformation mixture of cysteinsulfinic acid to pyruvic acid as caused by GOT. Through transformation coefficients it is possible to calculate, from the Δ E/min observed before and after the addition of cysteinsulfinic acid, the exact values of GOT and GPT enzymatic units present in the serum, by one only determination process.

EXAMPLE 2

Method of screening for determination of normal and pathological values of GOT and GPT activities in plasma or serum To a reaction mixture of 2.5 ml containing L-alanine (200 mM), α-ketoglutaric acid (2 mM), β-NADH (0.24 mM), cysteinsulfinic acid (7 mM) and 3.6. Units of lactic dehydrogenase in Tris-HCl buffer (50 mM), pH 8.5, 0.5 ml of serum or plasma are added and the extinction decrease is measured at 340 nm (or at other wave lengths, e.g. 334 or 365 nm, according to the instrument employed). In this case, the decrease of extinction is in direct relationship to the amount of transformation of both alanine and cysteinsulfinic acid to pyruvic acid, respectively caused by GPT and GOT, and it will be a measure of the sum of the two enzymatic activities. The kinetic characteristics of the assay permits one to establish a limit value of Δ E/min between normal and pathological values. Through opportune transformation coefficients it is possible, in the case of normal samples, to calculate exactly the actual enzymatic units of both GOT and GPT, while in the case of pathologic samples this method involves an error of about 10–15%.

We claim:

1. In a kinetic ultraviolet method for the determination of Glutamic Oxalacetic Transaminase (GOT) and Glutamic Pyruvic Transaminase (GPT) in serum or plasma in which transaminase is reacted with a substrate therefor and determining the reduction in ultraviolet absorbance of a revealing enzyme, the improvement which comprises employing L-cysteinsulfinic acid and L-alanine as the substrates for GOT and GPT, respectively, and using lactic dehydrogenase as the revealing enzyme for both transaminase activities, whereby a simultaneous determination of GOT and GPT in a single sample of serum or plasma can be effected.

2. The method according to claim 1 in which the total GOT and GPT transaminase activity is determined by determining the change in ultraviolet absorbance after reaction of the transaminase in the serum or plasma with both of said substrates.

3. The method according to claim 1 in which GPT is first determined by reacting transaminase in the serum or plasma with L-alanine as the substrate and determining the reduction in ultraviolet absorbance and then L-cysteinsulfinic acid is added and the resulting change in ultraviolet absorbance is determined, the latter change in ultraviolet absorbance being the measure of GOT transaminase activity.

4. A diagnostic kit for revealing normal or pathological values of Glutamic Oxalacetic Transaminase and Glutamic Pyruvic Transaminase including L-cysteinsulfinic acid and L-alanine as substrates for said transaminases, and lactic dehydrogenase as the revealing enzyme for both transaminase activities.

* * * * *